United States Patent [19]

Nehring et al.

[11] 4,195,633
[45] Apr. 1, 1980

[54] CHEST DRAINAGE SYSTEM WITH VISUAL FLOAT MEANS

[75] Inventors: John R. Nehring, Woodcliff Lake, N.J.; George E. King, Barrington, R.I.

[73] Assignee: International Paper Company, New York, N.Y.

[21] Appl. No.: 849,242

[22] Filed: Nov. 7, 1977

[51] Int. Cl.² ............................................. A61M 1/00
[52] U.S. Cl. ................................................... 128/276
[58] Field of Search ............... 128/275, 276, 277, 278, 128/208; 73/305, 309, 314, 315, 209, 208; 116/228

[56] References Cited

U.S. PATENT DOCUMENTS

| | | | |
|---|---|---|---|
| 793,177 | 6/1905 | Cady | 128/208 |
| 2,252,883 | 8/1941 | Everson | 73/209 |
| 2,400,097 | 5/1946 | Brewer | 73/209 |
| 3,381,687 | 5/1968 | Andersen et al. | 128/276 |
| 3,847,152 | 11/1974 | Schachet | 128/276 |
| 4,018,224 | 4/1977 | Kurtz et al. | 128/276 |

OTHER PUBLICATIONS

A New Measure of Safety in Chest Drainage-Sherwood Medical, 6 pages.

*Primary Examiner*—Robert W. Michell
*Assistant Examiner*—J. L. Kruter
*Attorney, Agent, or Firm*—Finnegan, Henderson, Farabow, Garrett & Dunner

[57] ABSTRACT

Disclosed is a chest drainage collection system including a suction control container, a water seal container, and at least one collection container. A first passage provides communication between the collection container and a patient's pleural cavity for communicating air and/or liquid to the collection container. A second passage provides communication between the seal container and the collection container. A third passage communicates between the suction control container and the seal container. A fourth passage communicates between a source of vacuum pressure and the water seal container. A float is disposed in the lower end of a tube in the water seal container to provide visual identification that the system is operational. A baffle overlies the water in the suction control container to preclude water entrainment and consequent water loss. The fourth passage contains a check valve for automatically sealing the fourth passage when the fourth passage is exposed to atmospheric pressure.

15 Claims, 5 Drawing Figures

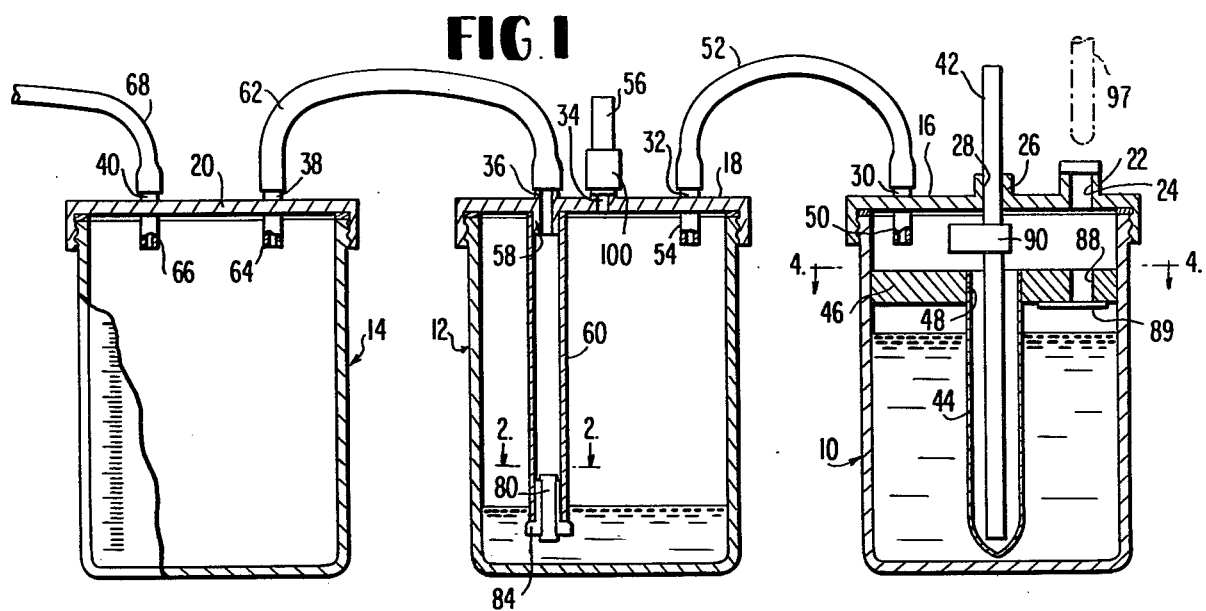
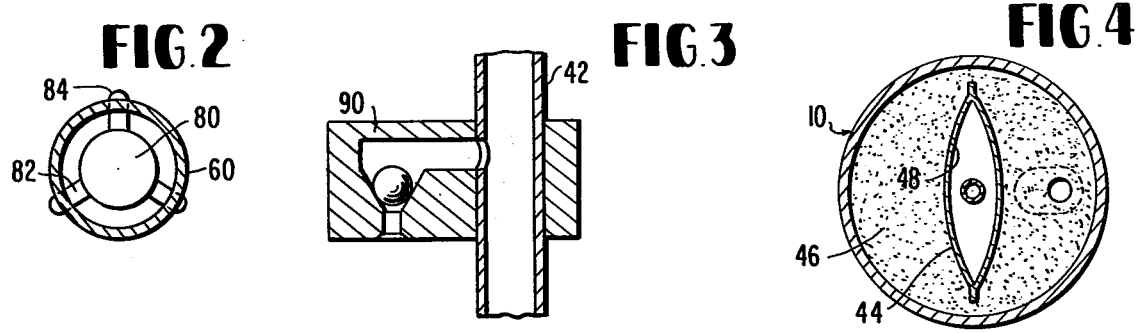
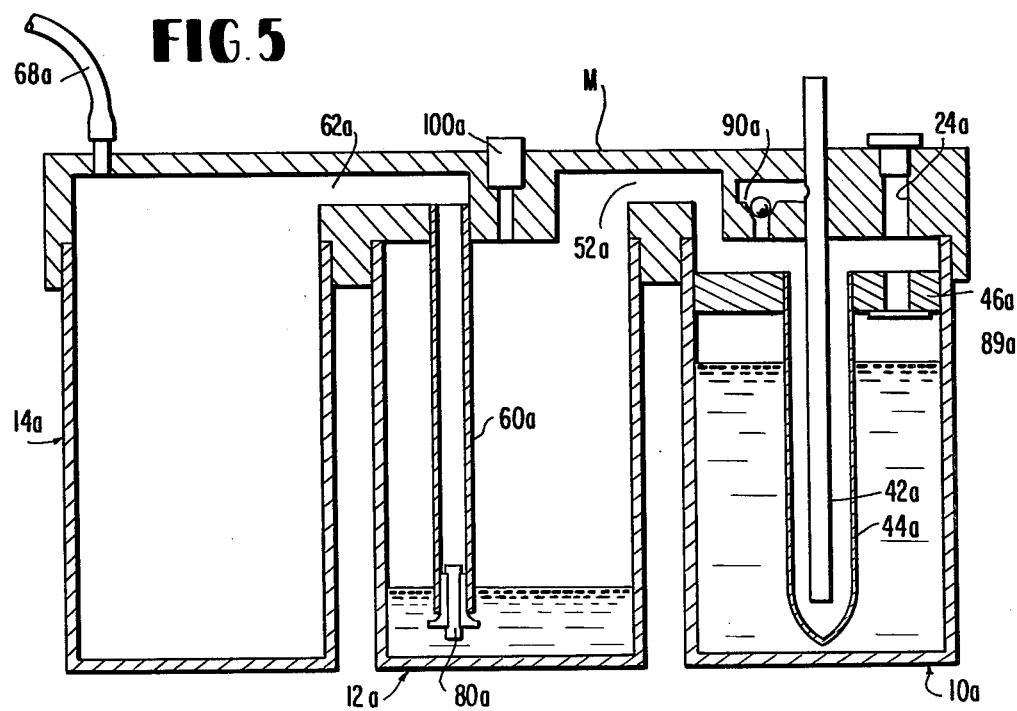

CHEST DRAINAGE SYSTEM WITH VISUAL FLOAT MEANS

The present invention relates to a drainage collection system and particularly relates to a novel and improved closed chest drainage system for the pleural cavity.

As is well known, it is sometimes necessary to drain fluids, i.e. gas, and/or liquid, from the pleural cavity. This can arise, for example as a result of a penetration of the chest wall, by surgical intervention, accident, or otherwise, which permits air and/or liquid to enter the pleural cavity. When air enters the pleural cavity, it raises the normal intrapleural pressure, thus rendering less effective the negative pressure developed by the enlargement of the chest cavity during inhalation, and also permits partial collapse of the lung. Consequently, it is necessary to take steps to reexpand the lung, restore the normal negative pressure in the lung cavity, and also to continuously vent or suction air and/or liquid from the pleural cavity. If these steps are not taken, air continues to enter the pleural cavity and, if it cannot escape, increases the pressure within the lung cavity. If pressure builds up sufficiently such that the pressure in the affected cavity is approximately 14 cm. of $H_2O$ greater than that in the unaffected cavity, a mediastinal shift can occur wherein the entire mediastinal area, including the heart and other tissues dividing the thoracic cavity, is pushed toward the lung cavity having the lower (normal) pressure. In this manner, an unaffected lung can collapse and/or heart action can be stopped. Consequently, it is of critical importance to prevent a positive buildup of pressure within the pleural cavity.

Conversely, it is equally important to prevent a high negative pressure condition in the pleural cavity, i.e. a pressure condition in which the pressure in the affected cavity is approximately 14 cm. of $H_2O$ less than that in the unaffected cavity. Otherwise, a mediastinal shift can occur toward the cavity containing the excessively high negative pressure.

Systems for draining fluids, i.e., gases and/or liquids, from the patient's pleural cavity are currently used routinely. For draining liquids, gravity drainage systems are sometimes utilized. In those systems, a chest catheter is placed in the pleural cavity with tubing leading below the level of water in the container. The stopper to the container has an air vent and the water acts as a one-way valve or seal to allow fluid from the patient's chest to flow through the tubing into the container but not to return.

More commonly, the classic three-bottle closed drainage system is employed for draining fluid, i.e., air and/or liquid, from a patient's pleural cavity. In that system, a suction control container, a water seal container and a collection container are interconnected by tubes extending through stoppers in the containers. A vacuum source is connected through the stopper of either the suction control container or the water seal container to maintain a negative pressure within the system. The suction control container carries a manometer tube which extends a specified distance below the level of water in the suction control container. The depth of the manometer tube in the suction control container controls the suction or negative pressure obtained in the system and in the pleural cavity. That is, the negative pressure in the system is a function of the head of water in the suction control container above the lower end of the manometer tube. In this classic three-bottle system, a tube from the collection bottle is connected with the patient's pleural cavity. Also, the tube interconnecting the water seal container and the collection container extends into the water seal container to a level slightly below the level of the water therein to form a water seal between the collection container and the water seal container. When this system obtains a negative pressure exceeding the desired suction pressure, air from the atmosphere flows into and through the suction control or manometer tube and bubbles through the water in the suction control container into the air space above the water to control and maintain the desired negative pressure in the system.

Many difficulties and disadvantages, however, are attendant in the use of the classical three-bottle system. These difficulties have been cured in significant part in an improved chest drainage system described and illustrated in copending Application Ser. No. 722,099 filed Sept. 10, 1976 abandoned Mar. 4, 1979 for CHEST DRAINAGE COLLECTION SYSTEM in the name of one of the coinventors herein. However, safeguards, in addition to those described in that application are believed necessary. For example, and in accordance with the present invention, it is desirable to enhance and visually magnify the excursion of the water within the water seal tube. It will be appreciated that small changes in pressure in the lung cavity can cause an almost imperceptible rise and fall of water within the water seal tube. This rise and fall of water within the water seal tube, however, is one way for attendants, and the patient as well, to monitor the system and to be satisfied that it is operating properly.

Thus, it is important to facilitate monitoring the rise and fall of the water in the tube such that it is readily and easily visually perceived. Consequently, and in accordance with the present invention, a float is disposed in the lower end of the water seal tube. The float can be solid or hollow, but in either case must have a specific gravity less than water. The float can be made of any soft material, e.g., polyethylene, polyvinylchloride, or polypropylene. Splines project laterally from the sides of the float for spacing it from the sides of the tube. The bottoms of the splines flare laterally outwardly to provide stops which prevent upward movement of the float in the tube beyond a predetermined elevation. The float can be colored, if desired, so that the level of the water in the tube is more readily observable. In this manner, the vertical and horizontal bobbing of the float enhances and visually magnifies the excursion of the water within the tube. The float may also provide an audible signal by periodically engaging the bottom of the water seal container or engaging its flared splines against the lower end of the water seal tube as gas escapes through the water seal. This further indicates that the system is operational.

Furthermore, it will be recalled from the above noted prior patent application, that a sleeve is disposed about the manometer tube in the suction control container to prevent bubbling of air from the atmosphere through the water and consequent loss of water by water entrainment in the air. It has been found that water loss can and does occur, however, due to the splashing action of the water against the sides of the container as a result of the fluttering action of the sleeve. That is, as the air enters the system the sleeve vibrates vigorously and these vibrations cause the water in the suction control bottle to splash against the sides of the container, a portion of that water being captured by the air exiting the sleeve.

In accordance with another feature of the present invention, there is provided an open cellular foam block disposed slightly above the water level in the suction control container and about the manometer tube and the outer sleeve. This prevents water droplets splashed against the sides of the suction control container as a result of the fluttering and vibrating action of the sleeve, as air passes into the system, from getting into the flow of air in the system. That is, it prevents the splashed water from being entrained with the air and being carried over into the water seal container. Also, by interposing an open cellular plastic block, only a nominal pressure drop, if any, is obtained across the block and accordingly the block does not interfere with the normal functioning of the system. Preferably, the block has an opening normally closed by a flap to enable insertion of a tube to withdraw water from the suction control container in the event that too much water is initially disposed in that container or it is desirable to reduce the level of suction.

Still further, it is important to safeguard against the development of high positive and negative pressures in the lung cavities with consequent prevention of pressure differences between the lung cavities which, if not relieved, would cause mediastinal shift. This is particularly significant when the drainage system is shifted from gravity to suction drainage or conversely from suction to gravity drainage or during patient transport when drainage is interrupted. During such times, this additional safeguard must prevent pressure differentials of approximately 14 cm. of $H_2O$ from developing between the two lung cavities in order to preclude mediastinal shift. For example, when a patient is being transported, it is common practice to disconnect the vacuum line from the vacuum source. The vacuum line is then either clamped or left open. When left open, it is possible for the pressure in the lung cavity to become sufficiently more negative such that water in the water seal container flows a substantial distance up the water seal tube. If the negative pressure is sufficient to draw water up the water seal tube to the extent that the end of the tube becomes exposed, air from the open vacuum line may enter the pleural cavity through the now open communication between the water seal and collection containers. This admission of air under atmospheric pressure can cause lung collapse and/or mediastinal shift.

In conventional three-bottle systems, the height of the water in the water seal container above the lower end of the water seal tube does not normally exceed 2 cm. of $H_2O$. This constitutes an upper limit, since a pressure head in excess of 2 cm. $H_2O$ can result in a positive back pressure in the pleural cavity which could cause lung collapse. If the water seal container is configured, however, such that the water is transferred to the collection container as a result of excessive negative pressure in the pleural cavity, air, if the vacuum tube is open, will eventually be admitted into the system and into the pleural cavity with deleterious and possibly fatal effects.

In accordance with a further aspect of the present invention, a valve automatically responsive to pressure substantially corresponding to atmospheric pressure is disposed in the vacuum tube line to close the vacuum tube line. Thus when the vacuum tube line is disconnected or malfunctions, the valve closes to prevent air from entering into the closed system through the vacuum line. Negative pressures will frequently develop in the lung cavity, however, when the system is closed. If this negative pressure becomes too high such that an approximately 14 cm. of $H_2O$ pressure differential obtains between the two lung cavities, a mediastinal shift can occur. It will be appreciated that by closing this valve, the pressure head developed in the water seal container and the pressure head of the suction control tube are placed in series, such that a negative pressure substantially equal to the pressure of the combined pressure heads must obtain in the collection chamber before atmospheric air can enter through the suction control or manometer tube into the otherwise closed system. The two pressure heads are set at a physiological level such that their sum is less than 14 cm. of $H_2O$ whereby air is permitted to enter the system before a mediastinal shift occurs due to excessive negative pressure.

Further to assist in setting the appropriate pressure heads, the water seal tube is provided with an increased inner diameter in comparison with the diameter of water seal tubes used in conventional three-bottle systems. That is, in conventional water seal tubes, the small interior diameter of the tube may allow a sufficient rise in the water level in the tube in response to high negative pressures to cause a mediastinal shift. By increasing the diameter of the water seal tube, this cannot occur since the lower end of the tube will first become exposed. This also precludes the likelihood of draining water from the water seal tube into the collection container. Stated differently, this limits the height of rise of the water within the water seal tube before the lower end of the tube is exposed to air. By enlarging the diameter of the water seal tube, it renders the disposition of a float in the water seal tube all the more necessary and significant since an enlarged diameter tube would cause even smaller visually perceptible changes in the rise and fall of the water in the tube. The float, however, compensates for this and increases the facility to monitor the operation of the system.

Further, in accordance with the present invention, a positive pressure relief valve is disposed in the suction control or manometer tube. Consequently, any pressure in the system in excess of approximately atmospheric pressure is vented. This also prevents mediastinal shift due to creation of a pressure differential in excess of 14 cm. of $H_2O$ as a result of positive pressure within the system.

Accordingly, it is a primary object of the present invention to provide a novel and improved chest drainage collection system.

It is another object of the present invention to provide a novel and improved chest drainage collection system having improved safety features including the provision of a float visualization indicator in the water seal tube to indicate the operability of the system.

It is still another object of the present invention to provide a novel and improved chest drainage collection system including a baffle to prevent loss of suction control water due to splashing of the water caused by air entering the system through the manometer tube.

It is a further object of the present invention to provide a novel and improved chest drainage collection system having improved safety features including prevention of mediastinal shift due to high differential pressures between the lung cavities as a result of either too high negative or positive pressures in one of the cavities.

It is a related object of the present invention to provide a novel and improved chest drainage collection system providing for ready interchangeability of the system between gravity and suction control drainage with improved safeguards to prevent lung collapse and/or mediastinal shift during changeover.

To achieve the foregoing objects and in accordance with the purposes of the invention, as embodied and broadly described herein, the chest drainage collection system of the present invention comprises a collection container, means carried by the collection container defining a first passage providing for communication between the collection chamber and a source of fluid to be collected external to the apparatus, a seal container, means defining a second passage between the collection container and the seal container providing for communication therebetween, means carried by the seal container for providing a fluid seal in the second passage, said fluid seal means including a tube in communication with said second passage and having a lower end disposed below the level of fluid in said water suction container, and a float disposed within the tube for increasing the visual perception of the rise and fall of the liquid within the tube, a suction control container, means defining a third passage between the suction control container and seal container providing for communication therebetween, means coupled to one of the suction control container and the seal container defining a fourth passage providing for communication between the one container and a source of vacuum pressure and, means carried by the apparatus for controlling the negative pressure within the containers when vacuum pressure is applied to the one container including means for communicating atmospheric air external to the apparatus into the suction container in response to a negative pressure within the suction control container greater than a predetermined negative pressure.

Preferably, and also in accordance with the present invention, there is a porous member disposed about the suction control tube in communication with said second passage and about the walls of said suction control container at an elevation slightly above the level of fluid in the suction control container for preventing entrainment of fluid in the air flowing into the apparatus. Also, a closure valve and a positive pressure relief valve are disposed in the fourth passage and the suction control tube respectively.

These and other objects and advantages of the present invention will become more apparent upon reference to the following specification, appended claims and drawings wherein:

FIG. 1 is a side elevational view of a novel and improved chest drainage system constructed in accordance with the present invention with parts broken out and in cross section for clarity;

FIG. 2 is a cross-sectional view thereof taken generally about on line 2—2 in FIG. 1;

FIG. 3 is an enlarged fragmentary cross-sectional view illustrating a positive pressure relief valve in the suction control tube of the suction control container illustrated in FIG. 1;

FIG. 4 is a cross-sectional view thereof taken generally about on line 4—4 in FIG. 1; and FIG. 5 is a longitudinal cross-sectional view of the novel and improved chest drainage collection system hereof incorporated in another embodiment hereof.

Referring now to FIG. 1, which illustrates a preferred embodiment of the present invention, there is illustrated a drainage collection system constructed in accordance with the present invention including a suction control container generally designated 10, a water seal container generally designated 12 and a collection container generally illustrated 14. Each container is generally cylindrical in shape (although other shapes could be utilized) having an open upper end which is closed by a cover or top. For example, covers 16, 18 and 20 are provided and may be screw-threaded onto the top of the suction control, water seal and collection containers 10, 12 and 14, respectively. These containers may be formed of any suitable material, preferably a clear plastic material such as Lexan or an equivalent polycarbonate resin, to minimize breakage and weight. The containers could also be formed of glass, if desired.

For reasons discussed hereinafter, cover 16 has three ports, a first normally closed nipple 22 defining a port 24, a second nipple 26 defining a port 28 and an opening defining a port 30. Cover 18 also has three ports 32, 34 and 36, whereas cover 20 has two ports 38 and 40.

Port 28 of suction control container 10 receives a suction control or manometer tube 42, the lower portion of which within container 10 is received within a flexible envelope 44 open at its upper end. For reasons discussed hereinafter, an open cellular block 46 is disposed within suction control tube 10 and the upper edge of the envelope or sleeve 44 may be secured about a central opening 48 in block 46. Alternatively, the upper end of sleeve 44 is open to the area in suction control container 10 above block 46. Port 30 includes a short tube 50 to which is attached one end of flexible tube 52, the opposite end of which is coupled to a tube 54 in port 32 of water seal container 12. Consequently, the interiors of suction control container 10 and water seal container 12 are in open communication one with the other through tubes 50, 52 and 54. An air line 56 is coupled to cover 18 about port 34, the opposite end of line 56 lying in communication with a source of vacuum pressure, not shown. Port 36 includes an interior nipple 58 to which the upper end of a depending water seal tube 60 is secured. The outer nipple about port 36 is secured to an end of a tubing 62, the opposite end of which is secured to a short tube 64 disposed in port 38 of collection container 14. Another tube 66 extends through port 40 and is attached at one end to a tube 68, the opposite end of which is for communication with the patient's pleural cavity.

Sleeve 44 is preferably formed of flexible material, such as a urethane film. A stand-off or inverted T-shaped element, not shown, may be disposed in the lower end of manometer tube 42 to prevent the lower portion of sleeve 44 from sealing about the lower end of tube 42.

In using the system described thus far, water is supplied to both the suction control container 10 and water seal container 12 to the appropriate levels. It will be appreciated that the height of the water in suction control container 10 above the lower end of manometer tube 42 defines a pressure head which, in turn, determines the suction pressure within the system. The level of water in the water seal container is slightly above the lower end of tube 60, and a water pressure head, for example, approximately 2 cm. of $H_2O$ is developed.

For gravity drainage, the vacuum tube line 56 is left open and the system is disposed below the elevation of the patient's pleural cavity. Consequently, liquid from the patient's pleural cavity is pumped by the natural breathing action of the patient into the collection chamber. Exhausted gases can escape from the system through the water seal and open port 24.

When suction pressure is desired, tube 56 is connected to a source of vacuum pressure, not shown. Thus suction pressure is provided in each container through the serially connected passages 62 and 52 and to the cavity to be drained. When a negative pressure develops within the suction control container 10 which exceeds the height of the water column between the lower end of tube 42 and the water level in the container 10, i.e. the water head above the lower end of tube 44, atmospheric air is admitted through passage 42 and into sleeve 44. The air entering the lower end of sleeve 44 through tube 42 rises within sleeve 44 out of contact with the water in suction control container 10 and exits into the air space or chamber above the water level in container 10. When the negative pressure in container 10 is equal to or decreases below the desired negative pressure, flexible sleeve 44 collapses and seals about tubing 42 whereupon the vacuum source reestablishes the vacuum level in the system at the desired negative pressure. Consequently, by use of sleeve 44, air flowing into the suction control container cannot entrain liquid particles or vapor during its passage into the container, since it is out of contact with the water in container 10 during passage. The air and/or liquid drained collects in the collection bottle 14 and the drained gases are removed by bubbling through the water seal water into the water seal container 12 and out through vacuum tube 56.

In accordance with the present invention, it will be appreciated that the visual perception of the rise and fall of the level of water in the water seal tube 60 is an indication of the proper operation of the system. That is, the normal breathing of the patient causes the water seal to fluctuate, i.e. rise and fall, within tube 60 according to the volume of air being forced in and out of the pleural cavity. This fluctuation can, however, be very small and not readily observable. Also, as noted hereinafter, the diameter of tube 60 is increased in comparison with the diameter of conventional water seal tubes. Thus, the rise and fall of the water level within the water seal tube in the present invention is much less perceptible in comparison with the water level fluctuations in prior smaller diameter water seal tubes.

In order to visualize and magnify small excursions of the water in tube 60, a float 80 is positioned within the lower end of tube 60. Preferably, the float is spaced from the inner walls of the lower end of tube 60 by a plurality of ribs 82 (FIG. 2). Float 80 is prevented from floating up through tube 60 by shoulders 84 which project diametrically from the lower ends of the splines 82. Shoulders 84 have sufficient radial extent to engage the lower end of tube 60 to prevent float 80 from moving up within the tube. The volume of the float in the tube causes a significant increase in the movement of the water within tube 60 and enhances the visibility of this fluctuation. The float acts as a bobber since it has a specific gravity less than water. It will be appreciated that the float can be colored to increase its visual perception. Further, the float can be hollow, if desired. Consequently, float 80 magnifies and provides for increased visibility of small excursions of the water in the water seal tube when small volumes of air are being moved through the system from the patient's pleural cavity. Also, the rise and fall of the float within the lower end of the tube 60 enables it to periodically engage the bottom of the container or to have its shoulders 84 engage the lower end of water seal tube 60 whereby an audible sound or signal indicating that the system is operating correctly is provided.

It will be appreciated that sleeve 44 vibrates or flutters as air enters the suction control container 10 causing the surface of the water to splash against the sides of container 10. To prevent entrainment of the water splashing against the sides of the container in the air flowing in the system, foam block 46 is disposed slightly above the level of fluid in the chamber below the block. Preferably, foam block 46 is an open cell foam disc whereby only a nominal pressure drop occurs across it. Thus, foam block 46 impedes or prevents droplets from this splashing from being entrained in the air flowing in the system without significantly affecting the pressure conditions in the system.

Foam block 46 has an opening 88 in registry below port 24 as illustrated in FIG. 4. Upon removal of the closure for port 24, a tube 97, illustrated by the dashed lines in FIG. 1, can be inserted through port 24 and opening 88 in block 46 whereby water can be added or removed from the suction control container 10 to adjust the suction as desired. A closure flap 89 normally seals about the underside of opening 88 closing it.

Referring now to FIG. 3, a positive pressure relief valve 90 is disposed in the suction control container 10 above block 46 for venting the system in the event that positive pressure, i.e. slightly above atmospheric pressure, is developed in the system. The valve 90 may comprise a check valve, for example a ball check valve as illustrated, in communication with manometer tube 42 and opening into the chamber above block 42. Consequently, ball check valve 90 normally seals the passage between manometer tube 42 and the chamber above block 46 in container 10, but valve 90 opens in response to a pressure in the system slightly above atmospheric pressure. This precludes the development of high positive pressures in the system and in the patient's pleural cavity which could result in lung collapse or mediastinal shift.

In accordance with a further aspect of this invention, a valve 100 is disposed in vacuum tube line 56 and which valve 100 closes in response to atmospheric pressure. Valve 100 is set to reopen at above about 5 inches of H$_2$O to assure a positive seal when the vacuum line is disconnected from the vacuum source. It will be appreciated that valve 100 can be located inside the water seal container 12 provided that it lies in communication with the vacuum line 56. When it is desired to switch from suction to gravity drainage or when the patient is to be transported and the vacuum line cannot be coupled to the vacuum source, the valve closes automatically upon disconnection of the vacuum line from the vacuum source.

Should the vacuum line be left open to the atmosphere, it will be appreciated that a negative pressure could develop in the pleural cavity in excess of the negative pressure necessary to raise the water level in water seal tube 60 sufficiently to expose the lower end of tube 60 to atmosphere. In this event, air would enter the pleural cavity causing partial lung collapse and/or mediastinal shift. Importantly, the closure of the vacuum tube line 56 by valve 100, places the pressure head in the water seal container 12 in series with the pressure head in suction control container 10. Consequently, before air can enter the system through manometer tube 42, a negative pressure in excess of these combined pressure heads must be obtained in the system. Since excessively high negative pressures in the pleural cavity can also cause lung collapse and/or mediastinal shift, the pressure heads are set at a physiological satisfactory value to preclude a pressure differential between the two lung cavities in excess of 14 cm. of $H_2O$. This physiological value is obtained in part by increasing the diameter of the inner tube 60 in water seal container 12 in comparison with the diameter of prior water seal tubes. This lowers its pressure head whereupon its pressure head combined with the pressure head in the suction control container can be set at the desired value. Also, this prevents loss of water seal fluid through tube 62 into the collection container in response to high negative pressures in the pleural cavity.

Referring now to FIG. 5, there are illustrated the various features of the present invention applied to the chest drainage system of the type described and illustrated in the foregoing noted patent application Ser. No. 722,099, filed Sept. 10, 1976. In this embodiment, like numerals are applied to like parts or parts which serve like functions as in the prior embodiment of FIG. 14 with the addition of letter suffixes. In the system disclosed in that application, a manifold M is provided to which discrete containers constituting the suction control, water seal and collection containers may be secured. Manifold M has passages 52a and 62a providing for intercommunication between the suction control container 10a and the water seal container 12a and the water seal container 12a and collection container 14a, respectively. Water seal tube 60a contains a float 80a similar to float 80 and a porous block 46a is disposed in the suction control chamber 10a similarly as block 46 is disposed in container 10 of the prior embodiment. Manifold M is also provided with an automatic shut-off valve 100a and a positive pressure relief valve 90a. This system functions similarly as previously described with respect to the embodiments of FIGS. 1-4 hereof and further description of its operation is not believed necessary. It is believed sufficient to note that the various features of the present invention are applicable to the invention disclosed in the prior application Ser. No. 722,099 filed Sept. 10, 1976, as those skilled in the art will appreciate.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by United States Letters Patent is:

1. Apparatus for collection of a fluid comprising:
    a collection container,
    means carried by said collection container defining a first passage providing for communication between said collection container and a source of fluid to be collected external to said apparatus,
    a transparent seal container for containing a fluid,
    means defining a second passage between said collection container and said seal container providing for communication therebetween,
    means carried by said seal container providing for a fluid seal in said second passage, said fluid seal means including a tube in communication with said second passage and having a lower end adapted to be disposed below the level of fluid in said seal container, and a float disposed within said tube for increasing the visual perception of the rise and fall of the fluid within the tube, said float having a plurality of ribs thereon for spacing the float from the inner walls of said tube,
    a suction control container for containing a fluid,
    means defining a third passage between said suction control container and said seal container providing for communication therebetween,
    means coupled to one of said suction control container and said seal container defining a fourth passage providing for communication between said one container and a source of vacuum pressure, and
    means carried by said suction control container for controlling the negative pressure within said containers when vacuum pressure is applied to said one container including means for communicating atmospheric air external to said apparatus into said suction control container in response to a negative pressure within said suction control container greater than a predetermined negative pressure.

2. Apparatus according to claim 1 wherein said float includes a plurality of shoulders projecting diametrically therefrom for engaging the lower end of said tube, for preventing movement of said float upwardly within said tube beyond a predetermined elevation and for providing an audible sound indicating correct system operation.

3. Apparatus according to claim 1 wherein said float is hollow.

4. Apparatus for collection of a fluid comprising:
    a collection container,
    means carried by said collection container defining a first passage providing for communication between said collection chamber and a source of fluid to be collected external to said apparatus,
    a seal container containing a fluid,
    means defining a second passage between said collection container and said seal container providing for communication therebetween,
    means carried by said seal container providing for a fluid seal in said second passage,
    a suction control container for containing a fluid,
    means defining a third passage between said suction control container and said seal container providing for communication therebetween,
    means coupled to one of said suction control container and said seal container defining a fourth passage providing for communication between said one container and a source of vacuum pressure,
    means carried by said apparatus for controlling the negative pressure within said containers when vacuum pressure is applied to said one container including a manometer tube having its lower end below the level of fluid in the suction control container for communicating atmospheric air external to said apparatus into said suction control container in response to a negative pressure within said suction control container greater than a predetermined negative pressure, and
    a porous member disposed about said tube and about the walls of said suction control container at an elevation slightly above the level of fluid in the suction control container for preventing entrainment of fluid in the air flowing into the apparatus.

5. Apparatus according to claim 4 wherein said member is comprised of an open cellular plastic foam.

6. Apparatus according to claim 4 wherein said member has an opening therethrough enabling entry of a tube into the fluid in the suction control container.

7. Apparatus according to claim 4 wherein said fluid seal means defines a first pressure head when the pressure in said collection container is sufficiently less than the pressure in said seal container to break said fluid seal and enable open communication through said second passage between said seal container and said collection container, wherein said negative pressure control means defines a second pressure head and a fifth passage for communicating atmospheric air external to said apparatus into said suction control container in response to a negative pressure within said suction control container more negative than said second predetermined pressure head, and valve means operationally connected with said fourth passage for closing said fourth passage and placing said first and second pressure heads in series one with the other such that a negative pressure substantially equal to the pressure of the combined pressure heads obtains in said collection apparatus before atmospheric air can communicate into said suction control container through said fifth passage, said closing means being responsive to sensing a pressure substantially about atmospheric pressure.

8. Apparatus according to claim 7 including a check valve in said suction control container for relieving pressure in said container in excess of about atmospheric pressure.

9. Apparatus according to claim 4 including a check valve in said suction control container for relieving pressure in said container in excess of about atmospheric pressure.

10. Apparatus for collection of a fluid comprising:
a collection container,
means carried by said collection container defining a first passage providing for communication between said collection container and a source of fluid to be collected external to said apparatus,
a transparent seal container containing a fluid,
means defining a second passage between said collection container and said seal container providing for communication therebetween,
means carried by said seal container providing for a fluid seal in said second passage, said fluid seal means including a tube in communication with second passage and having a lower end disposed below the level of fluid in said seal container, and a float disposed within said tube for increasing the visual perception of the rise and fall of the fluid within the tube,
a suction control container for containing a fluid,
means defining a third passage between said suction control container and said seal container providing for communication therebetween,
means coupled to one of said suction control container and said seal container defining a fourth passage providing for communication between said one container and a source of vacuum pressure, and
means carried by said suction control container for controlling the negative pressure within said containers when vacuum pressure is applied to said one container including means for communicating atmospheric air external to said apparatus into said suction control container in response to a negative pressure within said suction control container greater than a predetermined negative pressure, said negative pressure control means including a manometer tube disposed in said suction control container with its lower end at an elevation below the level of fluid in the suction control container, and a porous member disposed about said tube and about the walls of said suction control container at an elevation slightly above the level of fluid in the suction control container for preventing entrainment of the fluid in the air flowing into the apparatus.

11. Apparatus according to claim 10 wherein said member is comprised of an open cellular plastic foam.

12. Apparatus according to claim 11 wherein said member has an opening therethrough enabling entry of a tube into the fluid in the suction control container.

13. Apparatus according to claim 10 wherein said fluid seal means defines a first pressure head when the pressure in said collection container is sufficiently less than the pressure in said seal container to break said fluid seal and enable open communication through said second passage between said seal container and said collection container, wherein said negative pressure control means defines a second pressure head and a fifth passage for communicating atmospheric air external to said apparatus into said suction control container in response to a negative pressure within said suction control container more negative than said second predetermined pressure head, and valve means operationally connected with said fourth passage for closing said fourth passage and placing said first and second pressure heads in series one with the other such that a negative pressure substantially equal to the pressure of the combined pressure heads obtains in said collection apparatus before atmospheric air can communicate into said suction control container through said fifth passage, said closing means being responsive to sensing a pressure substantially about atmospheric pressure.

14. Apparatus according to claim 13 including a check valve in said suction control container for relieving pressure in said container in excess of about atmospheric pressure.

15. Apparatus according to claim 10 including a check valve in said suction control container for relieving pressure in said container in excess of about atmospheric pressure.

* * * * *